(12) United States Patent
Kobayashi et al.

(10) Patent No.: US 7,833,764 B2
(45) Date of Patent: Nov. 16, 2010

(54) DNA ENCODING XYLITOL DEHYDROGENASE

(75) Inventors: Osamu Kobayashi, Kanagawa (JP); Hideyuki Tamakawa, Kanagawa (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/525,417

(22) PCT Filed: Feb. 1, 2008

(86) PCT No.: PCT/JP2008/051676

§ 371 (c)(1),
(2), (4) Date: Jul. 31, 2009

(87) PCT Pub. No.: WO2008/093847

PCT Pub. Date: Aug. 7, 2008

(65) Prior Publication Data

US 2010/0093031 A1 Apr. 15, 2010

(30) Foreign Application Priority Data

Feb. 2, 2007 (JP) .............................. 2007-024666

(51) Int. Cl.
C12P 7/06 (2006.01)
C12N 1/00 (2006.01)
C12N 9/02 (2006.01)
C12N 15/00 (2006.01)
C07H 21/04 (2006.01)

(52) U.S. Cl. .................. 435/161; 435/189; 435/254.11; 435/254.21; 435/252.3; 435/320.1; 536/23.2; 536/23.1

(58) Field of Classification Search ........................ None
See application file for complete search history.

(56) References Cited

U.S. PATENT DOCUMENTS 6,582,944 B1 * 6/2003 Hallborn et al. ............. 435/161

FOREIGN PATENT DOCUMENTS

JP 2001-103988 4/2001
JP 2006-6213 1/2006

OTHER PUBLICATIONS

International Search Report PCT/JP2008/051676 dated Feb. 21, 2008.
Yong-su Jin et al., "Molecular Cloning of *XYL3* (D-Xylulokinase) from *Pichia stipitis* and Characterization of Its Physiological Function", Applied and Environmental Microbiology, vol. 68, No. 3, Mar. 2002, pp. 1232-1239.
Vina W. Wang et al., "Purification and Properties of Xylitol Dehydrogenase from the Xylose —Fermenting Yeast *Candida shehatae*", Applied Biochemistry and Biotechnology Nov. 1990, vol. 26, No. 2, pp. 197-206.

* cited by examiner

*Primary Examiner*—Nashaat T Nashed
(74) *Attorney, Agent, or Firm*—Stephen A. Bent; Foley & Lardner LLP

(57) ABSTRACT

The present invention relates to DNA encoding novel xylitol dehydrogenase and a method for using the same. Specifically, the present invention comprises providing the nucleic acid sequence of a xylitol dehydrogenase gene from *Candida shehatae* and introducing this gene into a host organism, thereby producing a microorganism having the ability to utilize xylose.

25 Claims, 3 Drawing Sheets

DNA ENCODING XYLITOL DEHYDROGENASE

TECHNICAL FIELD

The present invention relates to DNA encoding a polypeptide having a xylitol dehydrogenase activity, a nucleic acid construct and a vector comprising the DNA, a microorganism transformed with the vector to express the DNA, and a method for producing xylitol dehydrogenase. The microorganism, etc., of the present invention can be used in industrially useful steps such as ethanol production steps, biomass production steps, and steps of recycling $NADP^+$ from NADPH.

BACKGROUND ART

Xylose is a most abundant carbohydrate existing in plant biomass and lumber and constitutes approximately 40% of lignocellulose substances. Xylose, in cellulose production steps, is formed as waste products from hydrolysates of xylan, a main component of hemicellulose. It is desired for effective use of carbon resources that xylose should be converted to ethanol or biomass by fermentation. Particularly, ethanol is being used in large amounts as liquid fuel.

Candida (Gong, C. S., Chen, L. F., Flickinger, M. C. and Tsao, G. T., Conversion of hemicellulose carbohydrate. Adv. Biochem. Eng. 20: 93-118 (1981); and Jeffries, T. W., Utilization of xylose by bacteria, yeast and fungi. Adv. Biochem. Biotech. 27: 1-32 (1983)), Debaryomyces, Hansenula, Kluyveromyces, Metschnikowia, Pachysolen, Paecilomyces (Wu, J. F., Lastick, S. M., Updegraff, D. M., Ethanol production from sugars derived from plant biomass by a novel fungus. Nature 321: 887-888 (1986)), Pichia (Maleszka, R. and Schneider, H., Fermentation of D-xylose, xylitol and D-xylulose by yeasts. Can. J. Microbiol. 28: 360-363 (1982)), and the like are known as yeasts that can utilize pentose (e.g., xylose or D-ribose) or the like.

In general, the conversion of pentose (e.g., xylose) to ethanol in organisms is mediated by pentose phosphorylation, and the resulted phosphorylated pentose is converted to ethanol through a pentose phosphate pathway. The pentose phosphorylation first requires the reduction of pentose accompanied by conversion from NADPH to $NADP^+$, and this reaction is catalyzed by reductase. Pentitol, which is formed by the reduction of pentose, is subsequently subjected to oxidation accompanied by conversion from $NAD^+$ to NADH. This reaction is catalyzed by dehydrogenase. D-pentulose is formed through the two-step reaction and phosphorylated by kinase to form pentose phosphate (Barnett, J. A., The utilization of sugars by yeasts. In: Advances in carbohydrate chemistry and biochemistry; ed., by Tipson, R. S. and Horton, D.; New York: Academic Press. 1976, pp. 125-235).

S. cerevisiae, a yeast predominantly used in bioethanol production, can utilize xylulose (pentulose) converted from xylose, while this yeast cannot ferment pentoses (Jeffries, T. W., Emerging technology for fermenting D-xylose. Trends in Biotechnology 3: 208-212 (1985)). What is important is that S. cerevisiae contains genes encoding pentose-fermenting proteins but does not express these genes.

The pentose fermentation by S. cerevisiae is thought to be possibly achieved by providing a xylose utilization pathway from a microorganism that metabolizes xylose. Many attempts have been made on S. cerevisiae to express bacterial xylose isomerase genes, and xylose fermentation, however, has ended unsuccessfully, presumably due to insufficient expression of the foreign genes (Sartny, A. V., McConaugh, B. L., Lodo, Z., Sundstrom, J. A., Furlong, C. E. and Hall, B. D., Expression of the Escherichia coli xylose isomerase gene in Saccharomyces cerevisiae. Appi. Eur. Microbiol. 53: 1996-2000 (1987); Amoer, R., Wilhelm, M. and Hollenberg, C. P., The fermentation of xylose—an analysis of the expression of Bacillus and Actinoplanes xylose isomerase genes in yeast. Appl. Microbiol. Biotechnol. 30: 351-357 (1989); Chan, E.-C., Ueng, P. P. and Chen, L. F., D-xylose fermentation to ethanol by Schizosaccharomyces pombe cloned with xylose isomerase gene. Biotech. Lett. 8: 231-234 (1986); and Chan, E.-C., Ueng, P. P. and Chen, L. F., Environmental effects on D-xylose fermentation by Schizosaccharomyces cerevisiae. Appl. Biotechnol. 20: 221-232 (1989)).

On the other hand, attempts as methods using yeast genes in another yeast have been made to isolate xylose reductase- and xylitol dehydrogenase-encoding genes from Pichia stipitis which has the ability to utilize xylose, and to express the genes in S. cerevisiae (JP Patent Nos. 3122153 and 3193917). Moreover, attempts have been made on isolation of xylose reductase gene (Govinden, R., Pillay, B., van Zyl, W. H. and Pillay, D., Candida shehatae xylose reductase gene, complete cds., GenBank Direct Submission, Accession AF278715, (2000)) and purification of xylitol dehydrogenase (Yang, V. W. and Jeffries, T. W., Purification and properties of xylitol dehydrogenase from the xylose-fermenting yeast Candida shehatae. Appl. Biochem. Biotechnol., 26: 197-206 (1990)) from Candida shehatae, another yeast having the ability to utilize xylose. However, none of the cases have succeeded in isolating xylitol dehydrogenase genes from Candida shehatae.

DISCLOSURE OF THE INVENTION

An object of the present invention is to provide DNA encoding novel xylitol dehydrogenase, which can be used in the technology of efficient conversion of xylose to ethanol or biomass, and a method using the same.

SUMMARY OF THE INVENTION

The present invention has features below.

(1) A DNA encoding a polypeptide selected from:

(a) a polypeptide which comprises the amino acid sequence of SEQ ID NO: 1 and has a xylitol dehydrogenase activity;

(b) a polypeptide which comprises an amino acid sequence having 90% or higher identity to the amino acid sequence of SEQ ID NO: 1 and has a xylitol dehydrogenase activity; and (c) a polypeptide which comprises an amino acid sequence comprising substitution, deletion, insertion, or addition of one or several amino acids in the amino acid sequence of SEQ ID NO: 1 and has a xylitol dehydrogenase activity.

(2) The DNA according to (1), wherein the DNA comprises the nucleotide sequence of SEQ ID NO: 2.

(3) The DNA according to (1), wherein the DNA comprises a sequence that differs from the nucleotide sequence of SEQ ID NO: 2 due to the degeneracy of the genetic code.

(4) The DNA according to any of (1) to (3), wherein the DNA is from a yeast.

(5) The DNA according to (4), wherein the yeast is Candida shehatae.

(6) The DNA according to (5), wherein the yeast is Candida shehatae CBS5813 (NBRC1983).

(7) A nucleic acid construct comprising a DNA according to any of (1) to (6) and a regulatory sequence capable of regulating the expression of the DNA in a host cell.

(8) The nucleic acid construct according to (7), wherein the DNA encodes the amino acid sequence of SEQ ID NO: 1.

(9) The nucleic acid construct according to (8), wherein the DNA comprises the nucleotide sequence of SEQ ID NO: 2.

(10) The nucleic acid construct according to any of (7) to (9), wherein the regulatory sequence is from the host cell.

(11) The nucleic acid construct according to any of (7) to (9), wherein the regulatory sequence is a promoter.

(12) The nucleic acid construct according to (11), wherein the promoter is a constitutive promoter or an inducible promoter.

(13) The nucleic acid construct according to (11) or (12), wherein the promoter is selected from the group consisting of ADH1, ADH2, PDC, GAL1/10, TDH3, and PGK1 promoters.

(14) A vector comprising a DNA according to any of (1) to (6) or a nucleic acid construct according to any of (7) to (13).

(15) The vector according to (14), wherein the vector is a plasmid.

(16) A microorganism which comprises a DNA according to any of (1) to (6), a nucleic acid construct according to any of (7) to (13), or a vector according to (14) or (15), so that the microorganism expresses a polypeptide having a xylitol dehydrogenase activity.

(17) The microorganism according to (16), wherein the microorganism is a yeast or bacterium.

(18) The microorganism according to (17), wherein the yeast or bacterium is selected from the group consisting of yeasts of the genus *Saccharomyces, Schizosaccharomyces, Schwanniomyces, Kluyveromyces, Pichia, Hansenula, Candida, Debaryomyces, Metschnikowia, Pachysolen*, or *Paecilomyces*, and bacteria of the genus *Zymomonas*.

(19) The microorganism according to (18), wherein the microorganism is *Saccharomyces cerevisiae*.

(20) The microorganism according to (18), wherein the microorganism is *Schizosaccharomyces pombe*.

(21) The microorganism according to any one of (16) to (20), wherein the DNA or the nucleic acid construct is incorporated in the genome of the host microorganism.

(22) A method for producing xylitol dehydrogenase, comprising the steps of:

(a) culturing a microorganism according to any of (16) to (21) in a medium; and (b) collecting a product having a xylitol dehydrogenase activity from the microorganism or the medium.

(23) The method according to (22), further comprising the step of selecting a microorganism suitable for xylulose fermentation.

(24) A method for producing ethanol using a microorganism according to any of (16) to (21).

(25) A vector comprising a xylitol dehydrogenase gene expression cassette comprising a DNA according to (1), a xylose reductase gene expression cassette, and a xylulokinase gene expression cassette.

The present invention provides DNA encoding a xylitol dehydrogenase enzyme relating to xylulose fermentation, a microorganism (e.g., a yeast) recombinantly expressing the DNA, etc. The DNA and the microorganism are useful in bioethanol production, biomass production, food industry, and the like.

BEST MODE FOR CARRYING OUT THE INVENTION

Figure 1:
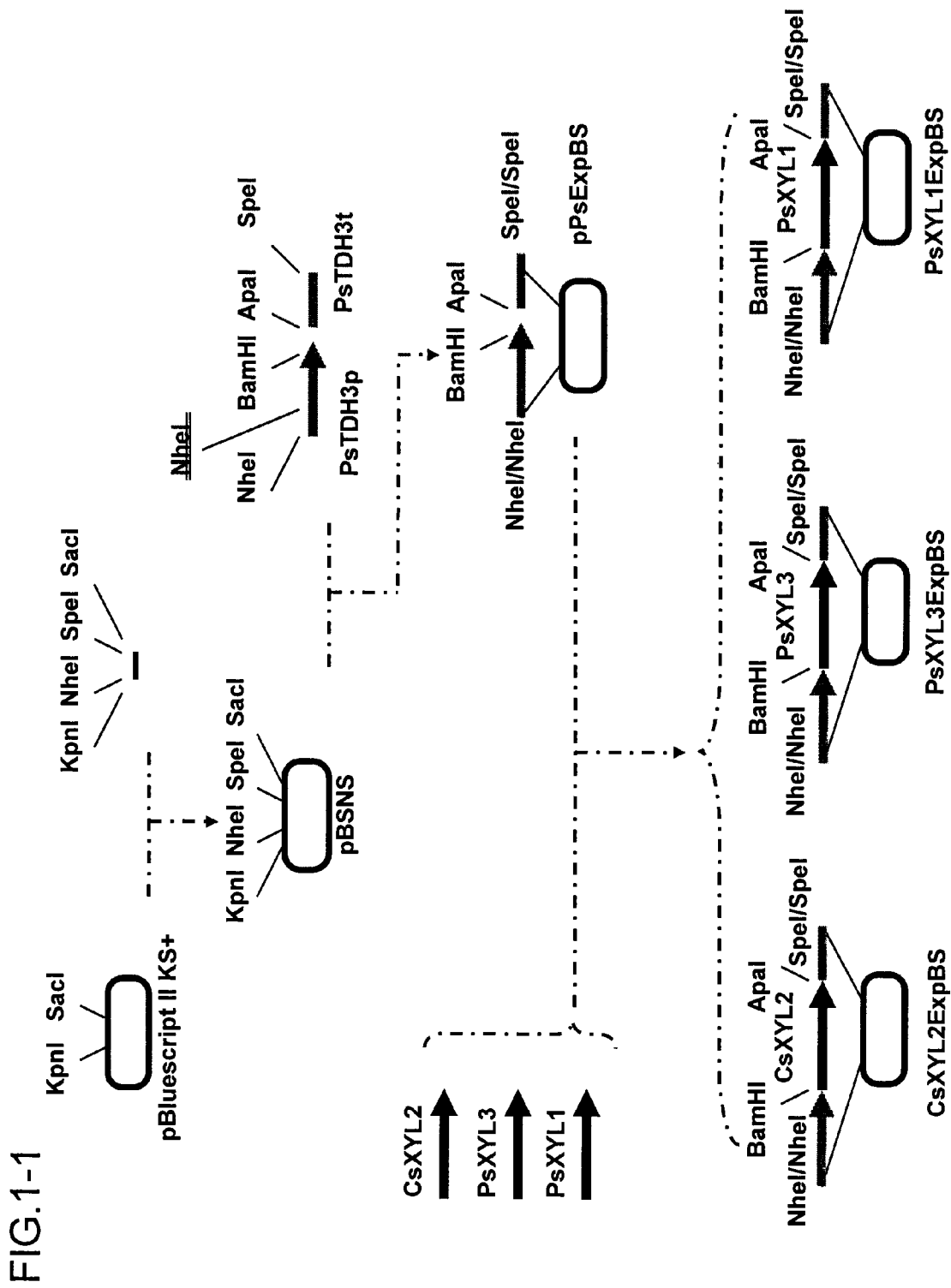
FIGS. 1-1 to 1-3 show an outline of procedures for constructing an expression vector comprising a xylitol dehydrogenase gene from *Candida Shehatae*.
Figures 1, 2:
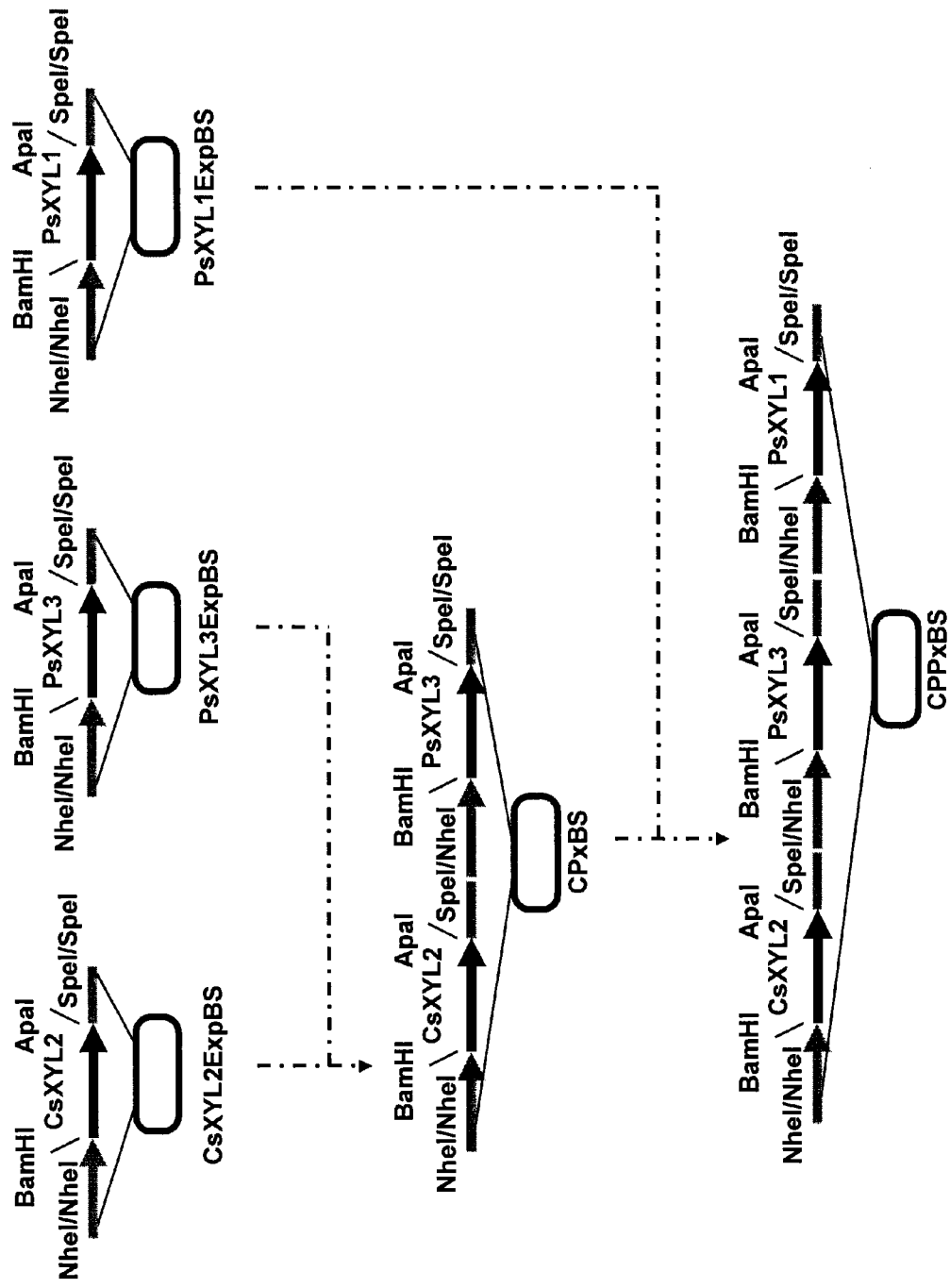
Figures 1, 2, 3:
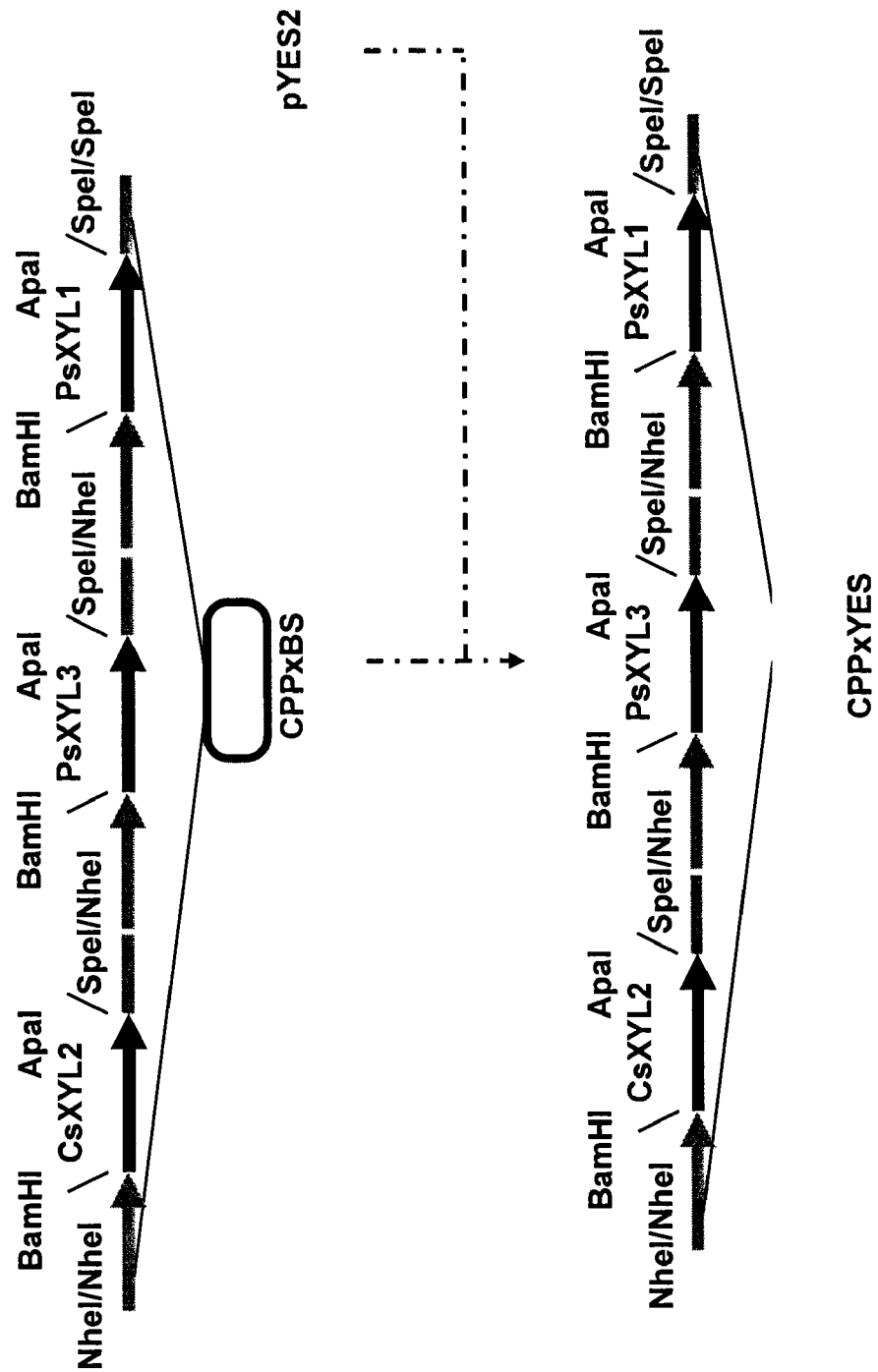

The present invention provides DNA encoding a polypeptide having a xylitol dehydrogenase activity.

Xylitol dehydrogenase (EC1.1.1.9) is an enzyme that catalyzes a part of a xylulose fermentation process using xylose as a raw material. The first half of the process is a reaction through which xylitol is reductively formed from xylose. This reductive reaction is catalyzed by a xylose reductase enzyme. The latter half of the process is a reaction through which xylulose is oxidatively formed from xylitol. This oxidative reaction is catalyzed by a xylitol dehydrogenase enzyme. The xylitol dehydrogenase activity is dependent on $NAD(P)^+$. Attempts have been made to introduce both xylose reductase and xylitol dehydrogenase genes into yeast (e.g., *Saccharomyces cerevisiae*) cells, thereby improving the ability to produce ethanol (e.g., U.S. Pat. No. 6,582,944).

The DNA of the present invention is a DNA encoding a polypeptide selected from:

(a) a polypeptide which comprises the amino acid sequence of SEQ ID NO: 1 and has a xylitol dehydrogenase activity;

(b) a polypeptide which comprises an amino acid sequence having 90% or higher identity to the amino acid sequence of SEQ ID NO: 1 and has a xylitol dehydrogenase activity; and (c) a polypeptide which comprises an amino acid sequence comprising substitution, deletion, insertion, or addition of one or several amino acids in the amino acid sequence of SEQ ID NO: 1 and has a xylitol dehydrogenase activity.

The DNA encoding the polypeptide of SEQ ID NO: 1 is from a yeast and specifically from *Candida shehatae*, particularly *Candida shehatae* CBS5813 (NBRC1983).

In the present invention, the polypeptide may consist of only the amino acid sequence of SEQ ID NO: 1 or can comprise said amino acid sequence as well as an additional sequence, for example, at the amino or carboxy terminus of the polypeptide. Such an additional amino acid sequence is, for example, a signal peptide sequence that provides extracellular secretion of mature proteins.

Alternatively, the polypeptide also encompasses a variant, homolog, analog, or the like, which comprises an amino acid sequence having 90% or higher identity to the amino acid sequence of SEQ ID NO: 1. In this context, the term "identity" means the proportion (%) of the number of completely matched amino acids to the total number of amino acids in the amino acid sequence aligned with or without gaps introduced therein. Such a polypeptide generally comprises an amino acid sequence comprising substitution, deletion, insertion, or addition of one or several amino acids in the amino acid sequence of SEQ ID NO: 1 and having, preferably 92% or higher or 93% or higher, more preferably 95% or higher or 97% or higher, even more preferably 98% or higher or 99% or higher sequence identity to said amino acid sequence.

The protein which has a sequence having 90% or higher identity thereto can be searched for, for example, by accessing a database known in the art (GenBank, EMBL, etc.). For example, an algorithm known in the art such as BLAST or FASTA can be used as a search system. Specific operation procedures for such a search are described in, for example, "Introduction to GenomeNet Databases", 2nd edition, ed. by Toshihisa Takagi and Minoru Kanehisa (1998), KYORITSU SHUPPAN CO., LTD (Tokyo, Japan).

Alternatively, the polypeptide also encompasses a variant which comprises an amino acid sequence comprising substitution, deletion, insertion, or addition of one or several amino acids in the amino acid sequence of SEQ ID NO: 1. In this context, the term "several" means an integer of approximately 10 or less, for example, an integer of 2 to 10, 2 to 9, 2 to 8, 2 to 7, 2 to 6, 2 to 5, 2 to 4, or 2 to 3.

The variant which comprises substitution, deletion, insertion, or addition of amino acids is encompassed within the scope of the present invention as long as it is novel and has a xylitol dehydrogenase activity.

The amino acid variation in the polypeptide encoded by the DNA of the present invention is preferably a mutation at a site that does not adversely affect, in the amino acid sequence of SEQ ID NO: 1, the three-dimensional structure (or conformation) of a catalytic domain associated with the xylitol dehydrogenase activity or a coenzyme-binding domain on which coenzymes act. However, a mutation can be introduced even in the catalytic domain or the coenzyme-binding domain unless it significantly reduces the enzyme activity. Examples of amino acids constituting the coenzyme-binding domain include $Asp^{207}$, $Ile^{208}$, $Phe^{209}$, $Asn^{211}$, and $Lys^{212}$ in the amino acid sequence of SEQ ID NO: 1. Examples of amino acids constituting the catalytic domain include $Cys^{41}$, $His^{66}$, $Glu^{67}$, $Ser^{96}$, $Ser^{99}$, $Tyr^{102}$, and $Cys^{110}$ in the amino acid sequence of SEQ ID NO: 1. Introduction of mutation(s) provides, for example, a variant having higher activity, for example, 1.5 times or more higher, 2 times or more higher, 2.5 times or more higher, 3 times or more higher, 5 times or more higher, 7 times or more higher, 10 times or more higher, 15 times or more higher, 20 times or more higher, 30 times or more higher, 40 times or more higher, or 50 times or more higher, than that of the wild type. Alternatively, introduction of mutation(s) can also improve a heat stability of the enzyme. Examples of the variation include variations as described in Watanabe, S. et al., J. Biol. Chem. 280 (11): 10340-10349 (2005).

Particularly, substitution between amino acids may be conservative substitution between amino acids similar in structural or chemical property or may be non-conservative substitution between amino acids differing in such a property. The amino acids similar in structural or chemical property can be classified as follows:

A hydrophobic amino acid group includes alanine, leucine, isoleucine, valine, methionine, and proline.

A polar amino acid group includes serine, threonine, glycine, glutamine, asparagine, and cysteine.

An aromatic amino acid group includes phenylalanine, tyrosine, and tryptophan.

An acidic amino acid group includes glutamic acid and aspartic acid.

A basic amino acid group includes lysine, arginine, and histidine.

The DNA of the present invention comprises single-stranded or double-stranded DNA having a nucleotide sequence encoding any of the polypeptides mentioned above. The DNA of the present invention encompasses, for example, natural DNA, cDNA, chemically synthesized DNA, DNA obtained by polymerase chain reaction (PCR), and DNA comprising two or more of these DNAs in combination.

Specifically, the DNA of the present invention is a DNA comprising the nucleotide sequence of SEQ ID NO: 2. Moreover, another DNA of the present invention is a DNA comprising a variant sequence of the nucleotide sequence of SEQ ID NO: 2 by the degeneracy of the genetic code. For example, an optimum codon for an organism species different from that as the origin of the wild type can be selected based on the degeneracy of the genetic code and included in the DNA. The variant sequence means a sequence comprising variations by which the resulted nucleotide sequence differs from the original nucleotide sequence although they encode the identical amino acid sequences.

The DNA of the present invention can be prepared using techniques known in the art such as DNA recombination, PCR, hybridization, cloning, and site-directed mutagenesis techniques. Such techniques are described in detail in, for example, Sambrook et al., Molecular Cloning: A Laboratory Manual, Cold Spring Harbor Laboratory Press, 1989 and Ausubel et al., Current Protocols in Molecular Biology, John Wiley & Sons, 1998 and may be used for the preparation of the DNA of the present invention.

First, *Candida shehatae* is grown, for example, by shaking culture at approximately 25° C. in a medium containing peptone, glucose, yeast extracts, and the like, such as YPD or YM medium, followed by genomic DNA extraction. Forward and reverse primers of 19 to 25 bases in length are designed and synthesized based on, for example, the nucleotide sequence of SEQ ID NO: 2. These primers are used to perform PCR amplification in the presence of thermostable polymerase and $Mg^{2+}$ using the genomic DNA of interest as a template. The PCR conditions involve performing, for example, treatment at 94° C. for 1 minute and subsequently approximately 35 amplification cycles each involving 94° C. for 30 seconds (denaturation), 55° C. for 30 seconds (annealing), and 72° C. for 3 minutes (elongation reaction), followed by final treatment at 72° C. for 7 minutes. The successful amplification of the DNA fragment of interest can be confirmed by agarose gel electrophoresis.

The amplified DNA fragment of interest is inserted, after introduction of appropriate restriction sites thereinto if necessary, into a vector (e.g., a plasmid), which is in turn introduced into an appropriate host cell to clone the DNA fragment. The vector can appropriately contain a promoter, a replication origin, a ribosome-binding site or Shine-Dalgarno sequence, a terminator, a multicloning site, a polyadenylation signal, and the like. Vectors for prokaryotes such as bacteria or vectors for eukaryotes such as yeasts or fungi can be used as the vector. Since various vectors are commercially available, appropriate one can be selected for use. Moreover, examples of the host cell include bacteria (e.g., *E. coli*) and yeasts.

The site-directed mutagenesis technique involves synthesizing a primer containing a variation site and performing PCR using this primer and, as a template, a vector containing the DNA of interest. The variant of the DNA comprising the nucleotide sequence of SEQ ID NO: 2 can be prepared by using this technique.

The present invention further provides a nucleic acid construct comprising the DNA described above and a regulatory sequence capable of regulating the expression of the DNA.

In the present invention, the regulatory sequence is a nucleotide sequence capable of regulating the expression of the DNA of the present invention and includes, for example, a promoter, an enhancer, a polyadenylation signal, a replication origin, a ribosome-binding site or Shine-Dalgarno sequence, and a terminator. The regulatory sequence is preferably a sequence containing a promoter or a sequence containing a terminator.

According to an embodiment of the present invention, the regulatory sequence is from the host cell. Particularly, when the 5'- and 3'-regulatory sequence-containing genomic sequence of a gene encoding xylitol dehydrogenase originally carried by a yeast as the host is allowed to flank the heterologous DNA of the present invention to prepare a vector, the heterologous DNA sequence of the present invention can be incorporated in the genome of the yeast cell by homologous recombination.

The promoter may be either a constitutive promoter or an inducible promoter. The promoter is not particularly limited and can be selected, for example, from the group consisting of ADH1, ADH2, PDC, GAL1/10, TDH3, and PGK1. Depending on the selected promoters (e.g., selected strong promoters), the DNA of the present invention may be expressed at an expression level exceeding the natural expression level in their original host microorganisms.

The present invention further provides a vector comprising any of the DNAs described above or any of the nucleic acid constructs described above.

Examples of the vector include plasmids, cosmids, phages, phagemids, BAC, YAC, and viruses. In a preferable embodiment, the vector is a plasmid. The vector is appropriate for replication in the desirable host microorganism and can thus contain, for example, a promoter, an enhancer, a polyadenylation signal, a replication origin, a ribosome-binding site or Shine-Dalgarno sequence, and a terminator, selected appropriately. Moreover, a selective marker such as a drug resistance gene (e.g., an ampicillin resistance gene) can be introduced in the vector.

The present invention also encompasses a vector comprising not only a xylitol dehydrogenase gene expression cassette but also optionally a xylulokinase gene expression cassette and/or a xylose reductase gene expression cassette. The xylitol dehydrogenase gene may be, for example, a DNA sequence encoding the polypeptide of SEQ ID NO: 1 or a DNA sequence encoding a variant, homolog, or analog of the polypeptide as described above. The xylulokinase gene may be, for example, a DNA sequence encoding the polypeptide of SEQ ID NO: 26 or a DNA sequence encoding a variant, homolog, or analog of the polypeptide as described above. The xylose reductase gene may be, for example, a DNA sequence encoding the polypeptide of SEQ ID NO: 24 or a DNA sequence encoding a variant, homolog, or analog of the polypeptide as described above.

In the present invention, the "expression cassette" is a nucleic acid construct that is prepared by operably linking the gene sequence of interest to a promoter and a terminator and other regulatory sequences necessary for the gene expression in a host. The construct is introduced into a host, thereby allowing the host to express the gene of interest. In the present invention, the term "operably linked" means that the regulatory sequences are linked to the gene of interest in such a manner that they are capable of acting on the expression of the gene of interest in the desired manner. Expression of each gene may be continuously or simultaneously. A construction example of such a vector of the present invention is shown in FIG. 1. This vector can be used effectively for ethanol production using xylose or the like as a raw material.

The present invention further provides a microorganism which comprises any of the DNAs described above, any of the nucleic acid constructs described above, or any of the vectors described above, so that the microorganism expresses a polypeptide having a xylitol dehydrogenase activity.

A routine approach such as transformation or transduction is used for introducing the vector into the microorganism cell. Such an approach encompasses, for example, calcium phosphate, electroporation, protoplast, and spheroplast methods.

Examples of the microorganism include, but not limited to, yeasts, fungi, and bacteria. Preferably, the microorganism is selected from the group consisting of yeasts of the genus *Saccharomyces, Schizosaccharomyces, Schwanniomyces, Kluyveromyces, Pichia, Hansenula, Candida, Debaryomyces, Metschnikowia, Pachysolen,* or *Paecilomyces,* and bacteria of the genus *Zymomonas.* Preferably, the microorganism is *Saccharomyces cerevisiae* or *Schizosaccharomyces pombe.*

For the microorganism, the DNA or the nucleic acid construct can be incorporated in genome of the host microorganism. Incorporation in the genome can be achieved by linking sequences from the genome of the host microorganism to upstream and downstream of the DNA or the nucleic acid construct. A method suitable for the nucleotide sequence incorporation in the host cell genome is generally known by those skilled in the art. The vector can also be located separately from the genome of the host cell in the cell. In this case, the vector should be capable of autonomously replicating.

The microorganism of the present invention can further contain DNA encoding another enzyme that mediates the conversion process from xylose to ethanol. The another enzyme is, for example, xylose reductase or xylulokinase, preferably xylose reductase. Such enzymes may be from a microorganism of the same origin as that of the xylitol dehydrogenase enzyme according to the present invention or may be from a microorganism of a different origin therefrom. Moreover, the microorganism may be subjected to mutation treatment for enhancing the enzyme activity or heat stability (e.g., the microorganism is irradiated with high-energy rays such as UV rays, gamma rays, or electron ion beams or treated with a chemical mutagen such as nitrosoguanidine, nitrosourea, or nitrous acid).

The present invention further provides a method for producing xylitol dehydrogenase. This method comprises the steps of: (a) culturing any of the microorganisms described above in a medium; and (b) collecting, from the microorganism or the medium, a product having a xylitol dehydrogenase activity. The collection of the product from the microorganism can be performed, for example, by ultrasonically disrupting the microorganism cell. The collection of the product from the medium requires, after translation into the polypeptide within the microorganism cell, extracellularly secreting this polypeptide. For this purpose, for example, the polypeptide can be expressed with an amino-terminal secretion signal linked thereto.

The conditions of the microorganism culture can be selected arbitrarily from among conditions suitable for the type of the microorganism. The medium generally contains a carbon source, a nitrogen source, and an inorganic salt. Examples of the carbon source include glucose, maltose, sucrose, lactose, starch, and other sugars. Examples of the nitrogen source include nitrogen-containing inorganic salts (e.g., ammonium sulfate and nitrate), peptone, malt extracts, and yeast extracts. Examples of the inorganic salt include alkaline metal salts, alkaline-earth metal salts, and salts of iron-group metals. The manners of culture encompass static culture, shaking culture, aeration culture, continuous culture, and the like. The culture temperature is approximately 15 to 60° C., usually approximately 25 to 40° C., though not limited to this range.

The activity of the formed enzyme can be measured, for example, by measuring NAD(P)$^+$ reduction at 340 nm at 35° C. (Rizzi, M. et al., J. Ferment. Bioeng. 67: 20-24 (1989)). The standard assay mixture is a solution containing 50 mM MgCl$_2$ and 300 mM xylitol dissolved in 50 mM Tris-HCl (pH 9.0). The reaction is initiated by the addition of 100 µl of 20 mM NAD(P)$^+$ at a final volume of 1.0 ml. The enzyme activity can be indicated, for example, using, as 1 unit, an enzyme activity that produces 1 µmol NAD(P)H per minute.

The xylitol dehydrogenase enzyme can be purified using general approaches of protein chemistry in combination. Examples of such approaches include, but not limited to, gel filtration, ion-exchange chromatography, affinity chromatography, hydrophobic interaction chromatography, HPLC, electrophoresis, isoelectric focusing, salting out, ammonium sulfate fractionation, dialysis, and ultrafiltration.

According to an embodiment of the present invention, the method can further comprise the step of selecting a microorganism suitable for efficient xylulose fermentation. As a result, a polypeptide that catalyzes xylulose fermentation more efficiently can be obtained. The xylulose fermentation efficiency is evaluated, for example, by culturing the microorganism in a xylose- or xylitol-containing medium for a given period and then measuring the concentration of xylose contained in the medium.

The present invention further provides a method for producing ethanol using any of the microorganisms described above. The microorganism may be immobilized on a solid phase that permits the microorganism growth. Examples of such a solid phase include, but not limited to, polymers such as polyurethane and derivatives thereof, and polysaccharides such as alginate and carrageenan.

A more preferable carbohydrate for ethanol production is xylose. Thus, *Saccharomyces cerevisiae, Schizosaccharomyces pombe*, and/or a *Zymomonas* strain capable of fermenting xylose are very advantageous for ethanol production. The yeast strains of the present invention have the ability to ferment a concentrated carbohydrate solution, a high level of ethanol resistance, and the ability to produce ethanol at an enhanced concentration. These yeast strains have high cell viability for repetitive recycling and exhibit pH and temperature resistances. In xylose production steps, xylose is formed as waste products from hydrolysates of xylan. Xylan is a main component of hemicellulose. Thus, the use of xylose for the production of ethanol and/or biomass is very advantageous. Furthermore, the introduction of a NAD(P)H-dependent xylose reductase gene into the microorganism of the present invention facilitates conversion from xylose to xylulose. In this case, for the reductive reaction, this xylose reductase enzyme is particularly suitable for, for example, carrying or recycling (from NADPH to NADP$^+$) the corresponding coenzymes in bioreactors for amino acid production.

EXAMPLES

The present invention will be further described with reference to Examples below. However, the scope of the present invention is not limited to them.

Example 1

Isolation and Sequencing of Xylitol Dehydrogenase Gene from *Candida shehatae* Isolation of Chromosomal DNA

*Candida shehatae* NBRC1983 (CBS5813) was purchased from Department of Biotechnology, National Institute of Technology and Evaluation. *Saccharomyces cerevisiae* ATCC60715 was purchased from American Type Culture Collection. These yeasts were separately grown by shaking culture in YPD medium (2% peptone, 1% yeast extracts, and 2% glucose) at 25° C. until a resting stage. Chromosomal DNAs were isolated therefrom using Dr. GenTLE (Takara Bio Inc., Otsu-shi, Shiga, Japan) according to the protocol included therein.

Determination of Nucleotide Sequence of *Candida shehatae* Xylitol Dehydrogenase Gene The DNA sequences of *Pichia stipitis* and *Candida tropicalis* xylitol dehydrogenases (accession Nos. DD278642 and DQ201637, respectively) were obtained from a nucleic acid sequence database GenBank and subjected to sequence comparison using gene analysis software Genetyx (Genetyx Corp., Tokyo, Japan) to obtain the sequences of SEQ ID NOs: 3 and 4 from the highly similar regions. These two sequences were used as primers to perform PCR using the *Candida shehatae* NBRC1983 chromosomal DNA as a template, TaKaRa Ex Taq (Takara Bio Inc.), and GeneAmp PCR System 9700 (Applied Biosystems Japan). The reaction program was as follows: 94° C. for 1 minute, (94° C. for 30 seconds, 55° C. for 30 seconds, and 72° C. for 3 minutes)×35 cycles, and 72° C. for 7 minutes. The obtained PCR product was electrophoresed on a 1% agarose gel. As a result, an amplified DNA fragment of approximately 900 bp in size was observed.

The fragment thus obtained was cloned using TOPO TA Cloning Kit (Invitrogen Corp., Tokyo, Japan). Plasmids were collected from the obtained transformant and subjected to a sequencing reaction using BigDye Terminator v3.1 Cycle sequencing Kit (Applied Biosystems Japan, Tokyo, Japan). The nucleotide sequence was determined using DNA Genetic Analyzer 3100 (Applied Biosystems Japan, Tokyo, Japan). The sequences of SEQ ID NOs: 5 and 6 were obtained from the resulted nucleotide sequence.

The *Candida shehatae* NBRC1983 chromosomal DNA was cleaved with various restriction enzymes and self-ligated, and the self-ligation products were collected by ethanol precipitation. PCR was performed using this product as a template, the sequences of SEQ ID NOs: 5 and 6 as primers, and TaKaRa LA Taq (Takara Bio Inc.). The reaction program was as follows: 94° C. for 1 minute, (98° C. for 20 seconds and 68° C. for 10 minutes)×30 cycles, and 72° C. for 7 minutes. The obtained PCR product was electrophoresed on a 1% agarose gel. As a result, an amplified DNA fragment of approximately 2300 bp in size was observed.

The fragment thus obtained was cloned using TOPO TA Cloning Kit (Invitrogen Corp., Tokyo, Japan). Plasmid were collected from the obtained transformant and subjected to a sequencing reaction using BigDye Terminator v3.1 Cycle sequencing Kit (Applied Biosystems Japan, Tokyo, Japan). The nucleotide sequence was determined using DNA Genetic Analyzer 3100 (Applied Biosystems Japan, Tokyo, Japan).

The obtained nucleotide sequence was assembled with the previously obtained nucleotide sequence of approximately 900 bp corresponding to the partial sequence of the xylitol dehydrogenase gene to obtain the nucleotide sequence of a coding region in the *Candida shehatae* xylitol dehydrogenase gene. The result is shown in SEQ ID NO: 2.

Example 2

Construction of Xylitol Dehydrogenase Expression Vector and Introduction Thereof into Yeast A xylitol dehydrogenase expression vector was constructed according to procedures shown in FIG. 1. Hereinafter, the construction will be described in detail. In this context, the PCR conditions described below are as follows: 94° C. for 1 minute, (94° C. for 30 seconds, 55° C. for 30 seconds, and 72° C. for 3 minutes)×35 cycles, and 72° C. for 7 minutes.

pBluescript II KS+ (Stratagene) was digested with KpnI and SacI, and the shorter fragment was removed using Chroma Spin TE100 (Invitrogen Corp.). On the other hand, the oligo DNAs of SEQ ID NOs: 7 and 8 were denatured by heating at 95° C. for 5 minutes and then left at room temperature for spontaneous annealing. This annealing product was cloned into the KpnI-SacI site in the pBluescript II KS+ to construct a vector pBSNS comprising NheI and SpeI sites inserted in between the KpnI and SacI sites of the pBluescript II KS+.

Primers (SEQ ID NOs: 17 and 18) for amplifying the *Candida shehatae* xylitol dehydrogenase gene were prepared based on the sequence of SEQ ID NO: 2. Oligo DNAs of SEQ ID NOs: 6 to 16, 19, and 20 were prepared based on the genomic sequence of *Pichia stipitis*.

A TDH3 promoter fragment (PsTDH3p) was obtained as follows: a combination of oligo DNAs of SEQ ID NOs: 9 and 10 and a combination of oligo DNAs of SEQ ID NOs: 11 and 12 were separately used as primers to perform PCR using the *Pichia stipitis* chromosomal DNA as a template. The primers were removed from respective obtained products using gel filtration columns. These two products were mixed and used as a template in PCR using oligo DNAs of SEQ ID NOs: 9 and 12 as primers to obtain a TDH3 promoter fragment. The obtained promoter fragment has NheI at the 5' end and BamHI and ApaI sites in this order at the 3' end and further, is free from NheI within the promoter sequence.

A TDH3 terminator fragment (PsTDH3t) was obtained by PCR using a combination of oligo DNAs of SEQ ID NOs: 13 and 14 as primers and *Pichia stipitis* chromosomal DNA as a template. The obtained terminator fragment has BamHI and ApaI sites in this order at the 5' end and a SpeI site at the 3' end.

These fragments are designed such that the 3' end of the TDH3 promoter fragment matches with the 5' end of the TDH3 terminator. These two fragments were mixed and used as a template in PCR using oligo DNAs of SEQ ID NOs: 9 and 14 as primers to prepare a fragment comprising the TDH3 promoter and the TDH3 terminator linked via BamHI and ApaI sites. The obtained fragment was inserted via a NheI site at the 5' end and a SpeI site at the 3' end to the NheI-SpeI site of the pBSNS to construct pPsExpBS.

PCR was performed using *Candida shehatae* chromosomal DNA as a template and oligo DNAs of SEQ ID NOs: 17 and 18 as primers to obtain a *Candida shehatae* xylitol dehydrogenase gene fragment (CsXYL2). PCR was performed using *Pichia stipitis* chromosomal DNA as a template and oligo DNAs of SEQ ID NOs: 15 and 16 as primers to obtain a *Pichia stipitis* xylose reductase gene fragment (PsXYL1; SEQ ID NO: 23). The amino acid sequence of a xylose reductase protein translated from the nucleotide sequence of the obtained DNA fragment is shown in SEQ ID NO: 24.

A *Pichia stipitis* xylulokinase gene fragment (PsXYL3; SEQ ID NO: 25) free from a XbaI site originally present within the sequence was obtained as follows: a combination of oligo DNAs of SEQ ID NOs: 19 and 20 and a combination of oligo DNAs of SEQ ID NOs: 21 and 22 were separately used as primers to perform PCR using the *Pichia stipitis* chromosomal DNA as a template. The primers were removed from respective obtained products using gel filtration columns. These two products were mixed and used as a template in PCR using oligo DNAs of SEQ ID NOs: 19 and 22 as primers to obtain *Pichia stipitis* xylulokinase gene fragment (PsXYL3; SEQ ID NO: 25). The amino acid sequence of a xylulokinase protein translated from the nucleotide sequence of the obtained DNA fragment is shown in SEQ ID NO: 26.

Each of the obtained gene fragments CsXYL2, PsXYL1, and PsXYL3 has a BamHI site at the 5' end and an ApaI site at the 3' end. Each gene fragment was inserted via these restriction sites into a BamHI-ApaI site of the vector pPsExpBS. The obtained vectors were designated as CsXYL2ExpBS, PsXYL1ExpBS, and PsXYL3ExpBS, respectively.

The CsXYL2ExpBS was digested with SpeI and subsequently subjected to a dephosphorylation reaction. A NheI-SpeI fragment (containing the PsXYL3 expression cassette) prepared from PsXYL3ExpBS was ligated to the SpeI site of the digested CsXYL2ExpBS to obtain a plasmid CPxBS comprising the PsXYL3 expression cassette inserted at 3' end of the CsXYL2 expression cassette in the same orientation. Next, CPxBS was digested with SpeI and subsequently subjected to a dephosphorylation reaction. A NheI-SpeI fragment (containing the PsXYL1 expression cassette) prepared from PsXYL1ExpBS was ligated to the SpeI site of the digested CPxBS to obtain a plasmid CPPxBS comprising the CsXYL2 expression cassette, the PsXYL3 expression cassette, and the PsXYL1 expression cassette inserted in this order in the same orientation.

CPPxBS was digested with NheI and SpeI, and the NheI-SpeI fragment containing the CsXYL2 expression cassette, the PsXYL3 expression cassette, and the PsXYL1 expression cassette was purified and inserted into SpeI site of pYES2 (Invitrogen Corp.) to obtain CPPxYES.

A ura3 variant strain KY1094 was obtained according to a standard method using Wine Yeast Kyokai No. 3 (the Brewing Society of Japan). CPPxYES or pYES2 was introduced into KY1094 by a lithium method. As a result, a *Saccharomyces cerevisiae* transformant comprising the vector (CPPxYES) comprising the CsXYL2 expression cassette, the PsXYL3 expression cassette, and the PsXYL1 expression cassette inserted in this order in the same orientation as well as a *Saccharomyces cerevisiae* transformant (control) comprising the vector pYES2 free from these expression cassette inserts was obtained.

Example 3

Measurement of Xylitol Dehydrogenase Activity

The obtained *Saccharomyces cerevisiae* transformants were subjected to xylitol dehydrogenase activity measurement as shown below.

For preculture, the strains were inoculated into 2 mL of SD-ura (2% glucose) per test tube and shaking-cultured at 25° C. for 24 hours. 200 μL of the preculture solution containing the strains was inoculated into 5 mL of SD-ura (2% glucose) per test tube and main-cultured at 120 rpm at 25° C. for 24 hours. After the culture, the yeasts were collected by centrifugation, washed with a 100 mM sodium phosphate buffer solution (pH 7.0), 1 mM EDTA, and 5 mM mercaptoethanol, and then resuspended in 1 mL of the same buffer solution. To this yeast suspension, 1 g of GLASS BEADS 212-300 microns (SIGMA) was added, and the yeasts were disrupted at 4° C. for 15 minutes using MIX-TOWER A14 (TAIYO). After centrifugation at 120 rpm at 4° C. for 5 minutes, the supernatant was collected and used as a crude enzyme solution. The crude enzyme solution was measured for its protein concentration by Bradford method. Bovine serum albumin was used as a standard protein.

A reaction was performed at 30° C. for 10 minutes in a reaction system containing 100 mM Tris-HCl (pH 8.0), 5 mM magnesium chloride, 3 mM NAD$^+$, 100 mM xylitol, and 5% (v/v) crude enzyme solution. The absorbance was measured at a wavelength of 340 nm. A calibration curve was prepared using NADH, and 1 unit of the enzyme activity was calculated as an enzyme level (specific activity) that produces 1 μmol NADH for 1 minute per mg protein. The result is shown below. In this context, the numeric value is indicated in mean±standard deviation from 9 lots.

TABLE 1

| Strain | Specific activity (μmol/min · mg protein) |
|---|---|
| CPP × YES | 1.878 ± 0.166 |
| pYES | 0.000 ± 0.008 |

The enzyme activity was detected only in the strain transformed with the vector carrying the expression cassettes including the *Candida shehatae* xylitol dehydrogenase gene.

This demonstrated that the protein expressed from the *Candida shehatae* xylitol dehydrogenase gene has a desired activity.

INDUSTRIAL APPLICABILITY

The DNA and the microorganism of the present invention are useful in bioethanol production, biomass production, food industry, and the like.

FREE TEXT IN SEQUENCE LISTING

SEQ ID NOS: 3, 4, and 7 to 22: primers

The invention claimed is:

1. An isolated nucleic acid comprising a sequence encoding
   (a) a polypeptide which comprises the amino acid sequence of SEQ ID NO: 1 and has a xylitol dehydrogenase activity; or
   (b) a polypeptide which comprises an amino acid sequence having 90% or higher identity to SEQ ID NO: 1 and has a xylitol dehydrogenase activity.

2. The isolated nucleic acid according to claim 1, wherein the nucleic acid comprises the nucleotide sequence of SEQ ID NO: 2.

3. The isolated nucleic acid according to claim 1, wherein the nucleic acid comprises a sequence that differs from the nucleotide sequence of SEQ ID NO: 2 due to the degeneracy of the genetic code.

4. The isolated nucleic acid according to any one of claims 1 to 3, wherein the nucleic acid is isolated from a yeast.

5. The isolated nucleic acid according to claim 4, wherein the yeast is *Candida shehatae*.

6. The isolated nucleic acid according to claim 5, wherein the yeast is *Candida shehatae* CBS5813 (NBRC1983).

7. A nucleic acid construct comprising an isolated nucleic acid according to claim 1 and a regulatory sequence capable of regulating the expression of the nucleic acid in a host cell.

8. The nucleic acid construct according to claim 7, wherein the nucleic acid encodes the amino acid sequence of SEQ ID NO: 1.

9. The nucleic acid construct according to claim 8, wherein the nucleic acid comprises the nucleotide sequence of SEQ ID NO: 2.

10. The nucleic acid construct according to any one of claims 7 to 9, wherein the regulatory sequence is from the host cell.

11. The nucleic acid construct according to any one of claims 7 to 9, wherein the regulatory sequence is a promoter.

12. The nucleic acid construct according to claim 11, wherein the promoter is a constitutive promoter or an inducible promoter.

13. The nucleic acid construct according to claim 11, wherein the promoter is selected from the group consisting of ADH1, ADH2, PDC, GAL1/10, TDH3, and PGK1 promoters.

14. A vector comprising an isolated nucleic acid according to claim 1 or a nucleic acid construct according to claim 7.

15. The vector according to claim 14, wherein the vector is a plasmid.

16. A microorganism transformed with the nucleic acid according to claim 1, the construct according to claim 7, or a vector comprising the nucleic acid or the construct.

17. The microorganism according to claim 16, wherein the microorganism is a yeast or bacterium.

18. The microorganism according to claim 17, wherein the yeast or bacterium is selected from the group consisting of yeasts of the genus *Saccharomyces, Schizosaccharomyces, Schwanniomyces, Kluyveromyces, Pichia, Hansenula, Candida, Debaryomyces, Metschnikowia, Pachysolen*, or *Paecilomyces*, and bacteria of the genus *Zymomonas*.

19. The microorganism according to claim 18, wherein the microorganism is *Saccharomyces cerevisiae*.

20. The microorganism according to claim 18, wherein the microorganism is *Schizosaccharomyces pombe*.

21. The microorganism according to claim 16, wherein the nucleic acid or the nucleic acid construct is incorporated in the genome of the host microorganism.

22. A method for producing xylitol dehydrogenase, comprising the steps of:
    (a) culturing a microorganism according to claim 16 in a medium; and
    (b) collecting a product having a xylitol dehydrogenase activity from the microorganism or the medium.

23. A method for producing xylitol dehydrogenase, comprising the steps of:
    selecting a microorganism according to claim 16 suitable for xylulose fermentation;
    culturing the microorganism in a medium; and
    collecting a product having a xylitol dehydrogenase activity from the microorganism or the medium.

24. A method for producing ethanol, comprising culturing a microorganism according to claim 16 in the presence of xylose, thereby producing ethanol.

25. A vector comprising a xylitol dehydrogenase gene expression cassette comprising an isolated nucleic acid according to claim 1, a xylose reductase gene expression cassette, and a xylulokinase gene expression cassette.

* * * * *

SEQUENCE LISTING

<160> NUMBER OF SEQ ID NOS: 26

<210> SEQ ID NO 1
<211> LENGTH: 364
<212> TYPE: PRT
<213> ORGANISM: Candida shehatae

<400> SEQUENCE: 1

```
Met Thr Ala Asn Pro Ser Leu Val Leu Asn Lys Ile Asp Asp Ile Thr
1               5                   10                  15

Phe Glu Ser Tyr Asp Ala Pro Glu Ile Thr Glu Pro Thr Asp Val Leu
            20                  25                  30

Val Glu Val Lys Lys Thr Gly Ile Cys Gly Ser Asp Ile His Tyr Tyr
        35                  40                  45

Ala His Gly Lys Ile Gly Asn Phe Val Leu Thr Lys Pro Met Val Leu
    50                  55                  60

Gly His Glu Ser Ser Gly Val Val Thr Lys Val Gly Thr Gly Val Thr
65                  70                  75                  80

Ser Leu Lys Val Gly Asp Lys Val Ala Ile Glu Pro Gly Ile Pro Ser
                85                  90                  95

Arg Phe Ser Asp Ala Tyr Lys Ser Gly His Tyr Asn Leu Cys Pro His
            100                 105                 110

Met Cys Phe Ala Ala Thr Pro Asn Ser Thr Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Glu His Val Ser Leu Glu Met Gly Ala Leu Val Glu Pro
145                 150                 155                 160

Leu Ser Val Gly Val His Ala Ser Lys Leu Ala Ser Val Arg Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Ile Asp Ile
        195                 200                 205

Phe Asp Asn Lys Leu Gln Met Ala Lys Asp Ile Gly Ala Ala Thr His
    210                 215                 220

Ile Phe Asn Ser Lys Thr Gly Gly Asp Ala Ala Ala Leu Val Lys Ala
225                 230                 235                 240

Phe Asp Gly Arg Glu Pro Thr Val Val Leu Glu Cys Thr Gly Ala Glu
                245                 250                 255

Pro Cys Ile Asn Gln Gly Val Ala Ile Leu Ala Gln Gly Gly Arg Phe
            260                 265                 270
```

```
Val Gln Val Gly Asn Ala Pro Gly Pro Val Lys Phe Pro Ile Thr Glu
        275                 280                 285

Phe Ala Thr Lys Glu Leu Thr Leu Phe Gly Ser Phe Arg Tyr Gly Phe
        290                 295                 300

Asn Asp Tyr Lys Thr Ser Val Asp Ile Met Asp Thr Asn Tyr Lys Asn
305                 310                 315                 320

Gly Lys Glu Lys Ala Pro Ile Asp Phe Glu Gln Leu Ile Thr His Arg
                325                 330                 335

Phe Lys Phe Asp Asp Ala Ile Lys Ala Tyr Asp Leu Val Arg Ala Gly
                340                 345                 350

Ser Gly Ala Val Lys Cys Ile Ile Asp Gly Pro Glu
        355                 360
```

<210> SEQ ID NO 2
<211> LENGTH: 1095
<212> TYPE: DNA
<213> ORGANISM: Candida shehatae

<400> SEQUENCE: 2

```
atgactgcta acccatcgct cgtgcttaac aagatcgacg acatcacctt cgagtcgtac      60
gatgccccag aaatcaccga gccaacagac gttctcgtgg aagtcaagaa aaccggtatc     120
tgtggttccg atatccacta ctacgcccac ggtaagatcg gtaacttcgt gttgaccaag     180
ccaatggttc ttggccacga atcctcaggt gtcgtcacca aggtcggtac cggcgtcacc     240
tcgctcaagg taggtgacaa ggtcgccatt gagccaggta ttccatccag attcagtgac     300
gcctacaaga gcggtcacta caacttatgt ccacacatgt gcttcgccgc cactccaaac     360
tccaccgagg gcgagccaaa cccaccaggt accttatgta agtacttcaa gtccccagag     420
gacttcttgg tcaagttgcc agaacacgtt tccttggaaa tgggtgctct tgtcgagcca     480
ttgtccgtcg gtgtccacgc ctccaagttg gcttccgtca gattcggtga ctacgtcgct     540
gttttcggtg ccggtccagt cggtctctta gctgctgccg tcgccaagac cttcggtgcc     600
aagggtgtca ttgtcattga catttttcgac aacaagttgc aaatggccaa ggacattggt     660
gctgctaccc acatcttcaa ctccaagacc ggtggtgacg ccgctgcctt ggtcaaggct     720
ttcgacggcc gcgagccaac cgtcgtcttg gaatgtactg gtgctgagcc atgtatcaac     780
caaggtgtcg ctatcttggc ccaaggtggt cgtttcgtcc aagtcggtaa cgccccaggt     840
ccagttaagt tcccaatcac tgaattcgct accaaggaac tcaccttgtt cggctctttc     900
agatacggtt tcaacgatta caagacctct gtcgacatca tggacaccaa ctacaagaac     960
ggtaaggaaa aggccccaat tgacttcgag caattgatca cccacagatt caagttcgac    1020
gacgccatca aggcctacga cttggtcaga gctggtagtg gtgctgtcaa gtgtatcatt    1080
gacggtcctg agtaa                                                     1095
```

<210> SEQ ID NO 3
<211> LENGTH: 25
<212> TYPE: DNA
<213> ORGANISM: Artificial
<220> FEATURE:
<223> OTHER INFORMATION: primer

<400> SEQUENCE: 3

```
agaaaaccgg tatctgtggt tccga                                            25
```

<210> SEQ ID NO 4
<211> LENGTH: 25

```
<212> TYPE: DNA
<213> ORGANISM: Artificial
<220> FEATURE:
<223> OTHER INFORMATION: primer

<400> SEQUENCE: 4
tgaacttgta tctgtgggtg atcaa                                          25

<210> SEQ ID NO 5
<211> LENGTH: 30
<212> TYPE: DNA
<213> ORGANISM: Candida shehatae

<400> SEQUENCE: 5
tagtggatat cggaaccaca gataccggtt                                     30

<210> SEQ ID NO 6
<211> LENGTH: 30
<212> TYPE: DNA
<213> ORGANISM: Candida shehatae

<400> SEQUENCE: 6
caattgatca cccacagata caagttcaaa                                     30

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
aaaaaaaaaa cgctagcccc gggactagtg agct                                34

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
cactagtccc ggggctagcg gtac                                           24

<210> SEQ ID NO 9
<211> LENGTH: 38
<212> TYPE: DNA
<213> ORGANISM: Artificial
<220> FEATURE:
<223> OTHER INFORMATION: primer

<400> SEQUENCE: 9
cggctagcga tgactctgta gaaagttgag tcaaatgc                            38

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
ctggaaagtg ctcgcaaaaa agcct                                          25

<210> SEQ ID NO 11
```

```
<211> LENGTH: 25
<212> TYPE: DNA
<213> ORGANISM: Artificial
<220> FEATURE:
<223> OTHER INFORMATION: primer

<400> SEQUENCE: 11 aggcttttt gcgagcactt tccag                                          25

<210> SEQ ID NO 12
<211> LENGTH: 45
<212> TYPE: DNA
<213> ORGANISM: Artificial
<220> FEATURE:
<223> OTHER INFORMATION: primer

<400> SEQUENCE: 12
tgttgggccc ttttggatcc gccgaaaccg ttaataccaa tcttg                   45

<210> SEQ ID NO 13
<211> LENGTH: 44
<212> TYPE: DNA
<213> ORGANISM: Artificial
<220> FEATURE:
<223> OTHER INFORMATION: primer

<400> SEQUENCE: 13
ggcggatcca aagggccca acacgttgcc aaggtttctg ctta                     44

<210> SEQ ID NO 14
<211> LENGTH: 33
<212> TYPE: DNA
<213> ORGANISM: Artificial
<220> FEATURE:
<223> OTHER INFORMATION: primer

<400> SEQUENCE: 14
ggactagtag gggtatccac ctattagtaa ttc                                33

<210> SEQ ID NO 15
<211> LENGTH: 37
<212> TYPE: DNA
<213> ORGANISM: Artificial
<220> FEATURE:
<223> OTHER INFORMATION: primer

<400> SEQUENCE: 15
cgggatccga ggtgaccgat ggggtgccaa ttaatgt                            37

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
cggggccccc ttcttagacg aagataggaa tcttgt                             36

<210> SEQ ID NO 17
<211> LENGTH: 35
<212> TYPE: DNA
<213> ORGANISM: Artificial
<220> FEATURE:
<223> OTHER INFORMATION: primer

<400> SEQUENCE: 17
```
cgggatccta gtccgctcta gttataccct acaaa                35

<210> SEQ ID NO 18
<211> LENGTH: 35
<212> TYPE: DNA
<213> ORGANISM: Artificial
<220> FEATURE:
<223> OTHER INFORMATION: primer

<400> SEQUENCE: 18
cggggcccgt ccaattattt actcaggacc gtcaa                35

<210> SEQ ID NO 19
<211> LENGTH: 35
<212> TYPE: DNA
<213> ORGANISM: Artificial
<220> FEATURE:
<223> OTHER INFORMATION: primer

<400> SEQUENCE: 19
cgggatccaa atactcacgt agttgacact cacaa                35

<210> SEQ ID NO 20
<211> LENGTH: 25
<212> TYPE: DNA
<213> ORGANISM: Artificial
<220> FEATURE:
<223> OTHER INFORMATION: primer

<400> SEQUENCE: 20
ctcggccgtt ctggaccagt atacc                25

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
ggtatactgg tccagaacgg ccga                24

<210> SEQ ID NO 22
<211> LENGTH: 33
<212> TYPE: DNA
<213> ORGANISM: Artificial
<220> FEATURE:
<223> OTHER INFORMATION: primer

<400> SEQUENCE: 22 cggggccta acgtctatcg tgatattcgc aca                33

<210> SEQ ID NO 23
<211> LENGTH: 957
<212> TYPE: DNA
<213> ORGANISM: Pichia stipitis
<220> FEATURE:
<221> NAME/KEY: CDS
<222> LOCATION: (1)..(957)
<220> FEATURE:
<223> OTHER INFORMATION: PsXYL1

<400> SEQUENCE: 23 atg cct tct att aag ttg aac tct ggt tac gac atg cca gcc gtc ggt        48
Met Pro Ser Ile Lys Leu Asn Ser Gly Tyr Asp Met Pro Ala Val Gly
1               5                   10                  15

-continued

```
ttc ggc tgt tgg aaa gtc gac gtc gac acc tgt tct gaa cag atc tac      96
Phe Gly Cys Trp Lys Val Asp Val Asp Thr Cys Ser Glu Gln Ile Tyr
         20                  25                  30 cgt gct atc aag acc ggt tac aga ttg ttc gac ggt gcc gaa gat tac     144
Arg Ala Ile Lys Thr Gly Tyr Arg Leu Phe Asp Gly Ala Glu Asp Tyr
 35                  40                  45 gcc aac gaa aag tta gtt ggt gcc ggt gtc aag aag gcc att gac gaa     192
Ala Asn Glu Lys Leu Val Gly Ala Gly Val Lys Lys Ala Ile Asp Glu
 50                  55                  60 ggt atc gtc aag cgt gaa gac ttg ttc ctt acc tcc aag ttg tgg aac     240
Gly Ile Val Lys Arg Glu Asp Leu Phe Leu Thr Ser Lys Leu Trp Asn
 65                  70                  75                  80 aac tac cac cac cca gac aac gtc gaa aag gcc ttg aac aga acc ctt     288
Asn Tyr His His Pro Asp Asn Val Glu Lys Ala Leu Asn Arg Thr Leu
             85                  90                  95 tct gac ttg caa gtt gac tac gtt gac ttg ttc ttg atc cac ttc cca     336
Ser Asp Leu Gln Val Asp Tyr Val Asp Leu Phe Leu Ile His Phe Pro
            100                 105                 110 gtc acc ttc aag ttc gtt cca tta gaa gaa aag tac cca cca gga ttc     384
Val Thr Phe Lys Phe Val Pro Leu Glu Glu Lys Tyr Pro Pro Gly Phe
            115                 120                 125 tac tgt ggt aag ggt gac aac ttc gac tac gaa gat gtt cca att tta     432
Tyr Cys Gly Lys Gly Asp Asn Phe Asp Tyr Glu Asp Val Pro Ile Leu
130                 135                 140 gag acc tgg aag gct ctt gaa aag ttg gtc aag gcc ggt aag atc aga     480
Glu Thr Trp Lys Ala Leu Glu Lys Leu Val Lys Ala Gly Lys Ile Arg
145                 150                 155                 160 tct atc ggt gtt tct aac ttc cca ggt gct ttg ctc ttg gac ttg ttg     528
Ser Ile Gly Val Ser Asn Phe Pro Gly Ala Leu Leu Leu Asp Leu Leu
                165                 170                 175 aga ggt gct acc atc aag cca tct gtc ttg caa gtt gaa cac cac cca     576
Arg Gly Ala Thr Ile Lys Pro Ser Val Leu Gln Val Glu His His Pro
            180                 185                 190 tac ttg caa caa cca aga ttg atc gaa ttc gct caa tcc cgt ggt att     624
Tyr Leu Gln Gln Pro Arg Leu Ile Glu Phe Ala Gln Ser Arg Gly Ile
            195                 200                 205 gct gtc acc gct tac tct tcg ttc ggt cct caa tct ttc gtt gaa ttg     672
Ala Val Thr Ala Tyr Ser Ser Phe Gly Pro Gln Ser Phe Val Glu Leu
210                 215                 220 aac caa ggt aga gct ttg aac act tct cca ttg ttc gag aac gaa act     720
Asn Gln Gly Arg Ala Leu Asn Thr Ser Pro Leu Phe Glu Asn Glu Thr
225                 230                 235                 240 atc aag gct atc gct gct aag cac ggt aag tct cca gct caa gtc ttg     768
Ile Lys Ala Ile Ala Ala Lys His Gly Lys Ser Pro Ala Gln Val Leu
                245                 250                 255 ttg aga tgg tct tcc caa aga ggc att gcc atc att cca aag tcc aac     816
Leu Arg Trp Ser Ser Gln Arg Gly Ile Ala Ile Ile Pro Lys Ser Asn
            260                 265                 270 act gtc cca aga ttg ttg gaa aac aag gac gtc aac agc ttc gac ttg     864
Thr Val Pro Arg Leu Leu Glu Asn Lys Asp Val Asn Ser Phe Asp Leu
            275                 280                 285 gac gaa caa gat ttc gct gac att gcc aag ttg gac atc aac ttg aga     912
Asp Glu Gln Asp Phe Ala Asp Ile Ala Lys Leu Asp Ile Asn Leu Arg
            290                 295                 300 ttc aac gac cca tgg gac tgg gac aag att cct atc ttc gtc taa        957
Phe Asn Asp Pro Trp Asp Trp Asp Lys Ile Pro Ile Phe Val
305                 310                 315
```

<210> SEQ ID NO 24

<211> LENGTH: 318
<212> TYPE: PRT
<213> ORGANISM: Pichia stipitis
<220> FEATURE:
<223> OTHER INFORMATION: PsXYL1

<400> SEQUENCE: 24

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 25
<211> LENGTH: 1872
<212> TYPE: DNA
<213> ORGANISM: Artificial
<220> FEATURE:
<221> NAME/KEY: CDS
<222> LOCATION: (1)..(1872)
<220> FEATURE:
<223> OTHER INFORMATION: PsXYL3_CDS_XbaI(-)

<400> SEQUENCE: 25

```
atg acc act acc cca ttt gat gct cca gat aag ctc ttc ctc ggg ttc      48
Met Thr Thr Thr Pro Phe Asp Ala Pro Asp Lys Leu Phe Leu Gly Phe
1               5                   10                  15 gat ctt tcg act cag cag ttg aag atc atc gtc acc gat gaa aac ctc      96
Asp Leu Ser Thr Gln Gln Leu Lys Ile Ile Val Thr Asp Glu Asn Leu
            20                  25                  30 gct gct ctc aaa acc tac aat gtc gag ttc gat agc atc aac agc tct     144
Ala Ala Leu Lys Thr Tyr Asn Val Glu Phe Asp Ser Ile Asn Ser Ser
        35                  40                  45 gtc cag aag ggt gtc att gct atc aac gac gaa atc agc aag ggt gcc     192
Val Gln Lys Gly Val Ile Ala Ile Asn Asp Glu Ile Ser Lys Gly Ala
    50                  55                  60 att att tcc ccc gtt tac atg tgg ttg gat gcc ctt gac cat gtt ttt     240
Ile Ile Ser Pro Val Tyr Met Trp Leu Asp Ala Leu Asp His Val Phe
65                  70                  75                  80 gaa gac atg aag aag gac gga ttc ccc ttc aac aag gtt gtt ggt att     288
Glu Asp Met Lys Lys Asp Gly Phe Pro Phe Asn Lys Val Val Gly Ile
                85                  90                  95 tcc ggt tct tgt caa cag cac ggt tcg gta tac tgg tcc aga acg gcc     336
Ser Gly Ser Cys Gln Gln His Gly Ser Val Tyr Trp Ser Arg Thr Ala
            100                 105                 110 gag aag gtc ttg tcc gaa ttg gac gct gaa tct tcg tta tcg agc cag     384
Glu Lys Val Leu Ser Glu Leu Asp Ala Glu Ser Ser Leu Ser Ser Gln
        115                 120                 125 atg aga tct gct ttc acc ttc aag cac gct cca aac tgg cag gat cac     432
Met Arg Ser Ala Phe Thr Phe Lys His Ala Pro Asn Trp Gln Asp His
    130                 135                 140 tct acc ggt aaa gag ctt gaa gag ttc gaa aga gtg att ggt gct gat     480
Ser Thr Gly Lys Glu Leu Glu Glu Phe Glu Arg Val Ile Gly Ala Asp
145                 150                 155                 160 gcc ttg gct gat atc tct ggt tcc aga gcc cat tac aga ttc aca ggg     528
Ala Leu Ala Asp Ile Ser Gly Ser Arg Ala His Tyr Arg Phe Thr Gly
                165                 170                 175 ctc cag att aga aag ttg tct acc aga ttc aag ccc gaa aag tac aac     576
Leu Gln Ile Arg Lys Leu Ser Thr Arg Phe Lys Pro Glu Lys Tyr Asn
            180                 185                 190 aga act gct cgt atc tct tta gtt tcg tca ttt gtt gcc agt gtg ttg     624
Arg Thr Ala Arg Ile Ser Leu Val Ser Ser Phe Val Ala Ser Val Leu
        195                 200                 205 ctt ggt aga atc acc tcc att gaa gaa gcc gat gct tgt gga atg aac     672
Leu Gly Arg Ile Thr Ser Ile Glu Glu Ala Asp Ala Cys Gly Met Asn
    210                 215                 220 ttg tac gat atc gaa aag cgc gag ttc aac gaa gag ctc ttg gcc atc     720
Leu Tyr Asp Ile Glu Lys Arg Glu Phe Asn Glu Glu Leu Leu Ala Ile
225                 230                 235                 240 gct gct ggt gtc cac cct gag ttg gat ggt gta gaa caa gac ggt gaa     768
Ala Ala Gly Val His Pro Glu Leu Asp Gly Val Glu Gln Asp Gly Glu
                245                 250                 255 att tac aga gct ggt atc aat gag ttg aag aga aag ttg ggt cct gtc     816
Ile Tyr Arg Ala Gly Ile Asn Glu Leu Lys Arg Lys Leu Gly Pro Val
            260                 265                 270 aaa cct ata aca tac gaa agc gaa ggt gac att gcc tct tac ttt gtc     864
Lys Pro Ile Thr Tyr Glu Ser Glu Gly Asp Ile Ala Ser Tyr Phe Val
        275                 280                 285 acc aga tac ggc ttc aac ccc gac tgt aaa atc tac tcg ttc acc gga     912
Thr Arg Tyr Gly Phe Asn Pro Asp Cys Lys Ile Tyr Ser Phe Thr Gly
    290                 295                 300 gac aat ttg gcc acg att atc tcg ttg cct ttg gct cca aat gat gct     960
Asp Asn Leu Ala Thr Ile Ile Ser Leu Pro Leu Ala Pro Asn Asp Ala
```

```
Asp Asn Leu Ala Thr Ile Ile Ser Leu Pro Leu Ala Pro Asn Asp Ala
305                 310                 315                 320 ttg atc tca ttg ggt act tct act aca gtt tta att atc acc aag aac    1008
Leu Ile Ser Leu Gly Thr Ser Thr Thr Val Leu Ile Ile Thr Lys Asn
                    325                 330                 335 tac gct cct tct tct caa tac cat ttg ttt aaa cat cca acc atg cct    1056
Tyr Ala Pro Ser Ser Gln Tyr His Leu Phe Lys His Pro Thr Met Pro
                340                 345                 350 gac cac tac atg ggc atg atc tgc tac tgt aac ggt tcc ttg gcc aga    1104
Asp His Tyr Met Gly Met Ile Cys Tyr Cys Asn Gly Ser Leu Ala Arg
            355                 360                 365 gaa aag gtt aga gac gaa gtc aac gaa aag ttc aat gta gaa gac aag    1152
Glu Lys Val Arg Asp Glu Val Asn Glu Lys Phe Asn Val Glu Asp Lys
        370                 375                 380 aag tcg tgg gac aag ttc aat gaa atc ttg gac aaa tcc aca gac ttc    1200
Lys Ser Trp Asp Lys Phe Asn Glu Ile Leu Asp Lys Ser Thr Asp Phe
385                 390                 395                 400 aac aac aag ttg ggt att tac ttc cca ctt ggc gaa att gtc cct aat    1248
Asn Asn Lys Leu Gly Ile Tyr Phe Pro Leu Gly Glu Ile Val Pro Asn
                    405                 410                 415 gcc gct gct cag atc aag aga tcg gtg ttg aac agc aag aac gaa att    1296
Ala Ala Ala Gln Ile Lys Arg Ser Val Leu Asn Ser Lys Asn Glu Ile
                420                 425                 430 gta gac gtt gag ttg ggc gac aag aac tgg caa cct gaa gat gat gtt    1344
Val Asp Val Glu Leu Gly Asp Lys Asn Trp Gln Pro Glu Asp Asp Val
            435                 440                 445 tct tca att gta gaa tca cag act ttg tct tgt aga ttg aga act ggt    1392
Ser Ser Ile Val Glu Ser Gln Thr Leu Ser Cys Arg Leu Arg Thr Gly
        450                 455                 460 cca atg ttg agc aag agt gga gat tct tct gct tcc agc tct gcc tca    1440
Pro Met Leu Ser Lys Ser Gly Asp Ser Ser Ala Ser Ser Ser Ala Ser
465                 470                 475                 480 cct caa cca gaa ggt gat ggt aca gat ttg cac aag gtc tac caa gac    1488
Pro Gln Pro Glu Gly Asp Gly Thr Asp Leu His Lys Val Tyr Gln Asp
                    485                 490                 495 ttg gtt aaa aag ttt ggt gac ttg ttc act gat gga aag aag caa acc    1536
Leu Val Lys Lys Phe Gly Asp Leu Phe Thr Asp Gly Lys Lys Gln Thr
                500                 505                 510 ttt gag tct ttg acc gcc aga cct aac cgt tgt tac tac gtc ggt ggt    1584
Phe Glu Ser Leu Thr Ala Arg Pro Asn Arg Cys Tyr Tyr Val Gly Gly
            515                 520                 525 gct tcc aac aac ggc agc att atc cgc aag atg ggt tcc atc ttg gct    1632
Ala Ser Asn Asn Gly Ser Ile Ile Arg Lys Met Gly Ser Ile Leu Ala
        530                 535                 540 ccc gtc aac gga aac tac aag gtt gac att cct aac gcc tgt gca ttg    1680
Pro Val Asn Gly Asn Tyr Lys Val Asp Ile Pro Asn Ala Cys Ala Leu
545                 550                 555                 560 ggt ggt gct tac aag gcc agt tgg agt tac gag tgt gaa gcc aag aag    1728
Gly Gly Ala Tyr Lys Ala Ser Trp Ser Tyr Glu Cys Glu Ala Lys Lys
                    565                 570                 575 gaa tgg atc gga tac gat cag tat atc aac aga ttg ttt gaa gta agt    1776
Glu Trp Ile Gly Tyr Asp Gln Tyr Ile Asn Arg Leu Phe Glu Val Ser
                580                 585                 590 gac gag atg aat ctg ttc gaa gtc aag gat aaa tgg ctc gaa tat gcc    1824
Asp Glu Met Asn Leu Phe Glu Val Lys Asp Lys Trp Leu Glu Tyr Ala
            595                 600                 605 aac ggg gtt gga atg ttg gcc aag atg gaa agt gaa ttg aaa cac taa    1872
Asn Gly Val Gly Met Leu Ala Lys Met Glu Ser Glu Leu Lys His
        610                 615                 620
```

<210> SEQ ID NO 26
<211> LENGTH: 623
<212> TYPE: PRT
<213> ORGANISM: Artificial
<220> FEATURE:
<223> OTHER INFORMATION: PsXYL3_CDS_XbaI(-)

<400> SEQUENCE: 26

```
Met Thr Thr Thr Pro Phe Asp Ala Pro Asp Lys Leu Phe Leu Gly Phe
1               5                   10                  15

Asp Leu Ser Thr Gln Gln Leu Lys Ile Ile Val Thr Asp Glu Asn Leu
            20                  25                  30

Ala Ala Leu Lys Thr Tyr Asn Val Glu Phe Asp Ser Ile Asn Ser Ser
        35                  40                  45

Val Gln Lys Gly Val Ile Ala Ile Asn Asp Glu Ile Ser Lys Gly Ala
    50                  55                  60

Ile Ile Ser Pro Val Tyr Met Trp Leu Asp Ala Leu Asp His Val Phe
65                  70                  75                  80

Glu Asp Met Lys Lys Asp Gly Phe Pro Phe Asn Lys Val Val Gly Ile
                85                  90                  95

Ser Gly Ser Cys Gln Gln His Gly Ser Val Tyr Trp Ser Arg Thr Ala
            100                 105                 110

Glu Lys Val Leu Ser Glu Leu Asp Ala Glu Ser Ser Leu Ser Ser Gln
        115                 120                 125

Met Arg Ser Ala Phe Thr Phe Lys His Ala Pro Asn Trp Gln Asp His
    130                 135                 140

Ser Thr Gly Lys Glu Leu Glu Phe Glu Arg Val Ile Gly Ala Asp
145                 150                 155                 160

Ala Leu Ala Asp Ile Ser Gly Ser Arg Ala His Tyr Arg Phe Thr Gly
                165                 170                 175

Leu Gln Ile Arg Lys Leu Ser Thr Arg Phe Lys Pro Glu Lys Tyr Asn
            180                 185                 190

Arg Thr Ala Arg Ile Ser Leu Val Ser Ser Phe Val Ala Ser Val Leu
        195                 200                 205

Leu Gly Arg Ile Thr Ser Ile Glu Glu Ala Asp Ala Cys Gly Met Asn
    210                 215                 220

Leu Tyr Asp Ile Glu Lys Arg Glu Phe Asn Glu Leu Leu Ala Ile
225                 230                 235                 240

Ala Ala Gly Val His Pro Glu Leu Asp Gly Val Glu Gln Asp Gly Glu
                245                 250                 255

Ile Tyr Arg Ala Gly Ile Asn Glu Leu Lys Arg Lys Leu Gly Pro Val
            260                 265                 270

Lys Pro Ile Thr Tyr Glu Ser Glu Gly Asp Ile Ala Ser Tyr Phe Val
        275                 280                 285

Thr Arg Tyr Gly Phe Asn Pro Asp Cys Lys Ile Tyr Ser Phe Thr Gly
    290                 295                 300

Asp Asn Leu Ala Thr Ile Ile Ser Leu Pro Leu Ala Pro Asn Asp Ala
305                 310                 315                 320

Leu Ile Ser Leu Gly Thr Ser Thr Thr Val Leu Ile Ile Thr Lys Asn
                325                 330                 335

Tyr Ala Pro Ser Ser Gln Tyr His Leu Phe Lys His Pro Thr Met Pro
            340                 345                 350

Asp His Tyr Met Gly Met Ile Cys Tyr Cys Asn Gly Ser Leu Ala Arg
        355                 360                 365
```

-continued

```
Glu Lys Val Arg Asp Glu Val Asn Glu Lys Phe Asn Val Glu Asp Lys
    370                 375                 380
Lys Ser Trp Asp Lys Phe Asn Glu Ile Leu Asp Lys Ser Thr Asp Phe
385                 390                 395                 400
Asn Asn Lys Leu Gly Ile Tyr Phe Pro Leu Gly Glu Ile Val Pro Asn
                405                 410                 415
Ala Ala Ala Gln Ile Lys Arg Ser Val Leu Asn Ser Lys Asn Glu Ile
            420                 425                 430
Val Asp Val Glu Leu Gly Asp Lys Asn Trp Gln Pro Glu Asp Asp Val
        435                 440                 445
Ser Ser Ile Val Glu Ser Gln Thr Leu Ser Cys Arg Leu Arg Thr Gly
    450                 455                 460
Pro Met Leu Ser Lys Ser Gly Asp Ser Ser Ala Ser Ser Ser Ala Ser
465                 470                 475                 480
Pro Gln Pro Glu Gly Asp Gly Thr Asp Leu His Lys Val Tyr Gln Asp
                485                 490                 495
Leu Val Lys Lys Phe Gly Asp Leu Phe Thr Asp Gly Lys Lys Gln Thr
            500                 505                 510
Phe Glu Ser Leu Thr Ala Arg Pro Asn Arg Cys Tyr Tyr Val Gly Gly
        515                 520                 525
Ala Ser Asn Asn Gly Ser Ile Ile Arg Lys Met Gly Ser Ile Leu Ala
    530                 535                 540
Pro Val Asn Gly Asn Tyr Lys Val Asp Ile Pro Asn Ala Cys Ala Leu
545                 550                 555                 560
Gly Gly Ala Tyr Lys Ala Ser Trp Ser Tyr Glu Cys Glu Ala Lys Lys
                565                 570                 575
Glu Trp Ile Gly Tyr Asp Gln Tyr Ile Asn Arg Leu Phe Glu Val Ser
            580                 585                 590
Asp Glu Met Asn Leu Phe Glu Val Lys Asp Lys Trp Leu Glu Tyr Ala
        595                 600                 605
Asn Gly Val Gly Met Leu Ala Lys Met Glu Ser Glu Leu Lys His
    610                 615                 620
```